United States Patent
Kopperschmidt

(10) Patent No.: US 8,177,736 B2
(45) Date of Patent: May 15, 2012

(54) DEVICE AND METHOD FOR MONITORING ACCESS TO A PATIENT, IN PARTICULAR ACCESS TO VESSELS DURING EXTRACORPOREAL BLOOD TREATMENT

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 727 days.

(21) Appl. No.: 12/282,568

(22) PCT Filed: Dec. 8, 2006

(86) PCT No.: PCT/EP2006/011810
§ 371 (c)(1),
(2), (4) Date: Dec. 18, 2008

(87) PCT Pub. No.: WO2007/104350
PCT Pub. Date: Sep. 20, 2007

(65) Prior Publication Data
US 2009/0306574 A1    Dec. 10, 2009

(30) Foreign Application Priority Data
Mar. 11, 2006 (DE) .......... 10 2006 011 313

(51) Int. Cl.
| A61M 37/00 | (2006.01) |
| A61M 1/00 | (2006.01) |
| A41F 1/00 | (2006.01) |
| A41F 1/08 | (2006.01) |
| A44B 1/04 | (2006.01) |
| A44B 1/18 | (2006.01) |
| A44B 11/25 | (2006.01) |
| A44B 17/00 | (2006.01) |
| B42F 1/00 | (2006.01) |
| F16D 1/08 | (2006.01) |
| F16D 3/80 | (2006.01) |
| F16L 17/00 | (2006.01) |

(52) U.S. Cl. ..................... 604/6.16; 604/4.01; 604/6.01; 604/317; 24/335; 24/455; 24/518; 403/31

(58) Field of Classification Search ................. 604/4.1, 604/6.1; 24/129 R, 130, 335, 336, 339, 545, 24/546, 570, 910
See application file for complete search history.

(56) References Cited

U.S. PATENT DOCUMENTS
1,816,301 A * 7/1931 Sundell .................. 24/339
(Continued)

FOREIGN PATENT DOCUMENTS
DE            4432348 C2      2/1995
(Continued)

OTHER PUBLICATIONS
Qu, Yongquan; Carter, Joshua; Guo, Tina. Silica Nanocoils. J. Phys. Chem. B 2006, 110, 8296-8301.*
(Continued)

*Primary Examiner* — Tatyana Zalukaeva
*Assistant Examiner* — Xin Xie
(74) *Attorney, Agent, or Firm* — Kenyon & Kenyon LLP

(57) ABSTRACT

The invention relates to a device and to a method for monitoring access to vessels during extracorporeal blood treatment. The invention forms a loop in the arterial and/or venous line and provides device for fixing a section of the line in a loop. When the line is stressed under tension, the loop contracts and the line finally kinks. The modification of the diameter of the line and the formation of a kink in the line leads to a rise of pressure in the line, which is monitored by a pressure monitoring device. If the pressure exceeds a predetermined threshold value, the aspirating cannula is in danger of slipping out of the vessel access or has partially or completely slipped out, thus allowing the threshold value to be determined for alarms.

19 Claims, 8 Drawing Sheets

U.S. PATENT DOCUMENTS

| | | | | |
|---|---|---|---|---|
| 2,723,431 A | * | 11/1955 | Di Renzo | 24/301 |
| 3,096,551 A | * | 7/1963 | Shoberg | 24/132 R |
| 3,521,332 A | * | 7/1970 | Kramer | 403/188 |
| 4,406,042 A | | 9/1983 | McPhee | |
| 4,425,114 A | * | 1/1984 | Schoendorfer et al. | 604/7 |
| 4,511,081 A | * | 4/1985 | Wilson | 238/59 |
| 4,707,906 A | * | 11/1987 | Posey | 29/453 |
| 5,205,687 A | * | 4/1993 | Boyland | 410/98 |
| 5,309,604 A | * | 5/1994 | Poulsen | 24/16 R |
| 5,368,281 A | * | 11/1994 | Skyba | 254/391 |
| 5,531,685 A | * | 7/1996 | Hemmer et al. | 604/95.05 |
| 5,578,003 A | | 11/1996 | Borger | |
| 5,803,484 A | * | 9/1998 | Orme | 280/728.2 |
| 5,826,621 A | | 10/1998 | Jemmott | |
| 6,012,204 A | * | 1/2000 | Roethler | 24/129 R |
| 6,061,880 A | * | 5/2000 | Senninger | 24/339 |
| 6,105,218 A | * | 8/2000 | Reekie | 24/518 |
| 6,113,577 A | | 9/2000 | Hakky et al. | |
| 6,158,095 A | * | 12/2000 | Lassiter | 24/339 |
| 6,652,561 B1 | * | 11/2003 | Tran | 606/232 |
| 6,691,382 B1 | * | 2/2004 | Su | 24/545 |
| 2001/0007930 A1 | | 7/2001 | Kleinekofort | |
| 2002/0120224 A1 | * | 8/2002 | Zia et al. | 604/6.16 |
| 2004/0098053 A1 | * | 5/2004 | Tran | 606/232 |
| 2006/0293710 A1 | * | 12/2006 | Foerster et al. | 606/232 |
| 2009/0048563 A1 | * | 2/2009 | Ethelfeld et al. | 604/174 |

FOREIGN PATENT DOCUMENTS

| | | |
|---|---|---|
| DE | 19959965 A1 | 6/2000 |
| DE | 19953068 A1 | 6/2001 |
| DE | 69720744 | 3/2004 |
| FR | 1306369 A | 10/1962 |
| GB | 2046095 A | 11/1980 |
| WO | 2004/020038 A | 3/2004 |

OTHER PUBLICATIONS

PCT/EP2006/011810 International Search Report, mailed Mar. 21, 2007.

* cited by examiner

DEVICE AND METHOD FOR MONITORING ACCESS TO A PATIENT, IN PARTICULAR ACCESS TO VESSELS DURING EXTRACORPOREAL BLOOD TREATMENT

CROSS REFERENCE TO RELATED APPLICATIONS

This is a 371 national phase application of PCT/EP2006/011810 filed 8 Dec. 2006, claiming priority to German Patent Application No. 10 2006 011 313.6 filed 11 Mar. 2006, the contents of which are incorporated herein by reference in its entirety.

FIELD OF INVENTION

The invention relates to a device for monitoring access to a patient of an apparatus for delivering a fluid to the patient or removing fluid from the patient via a hose line. In particular, the invention relates to a device for monitoring vascular access in extracorporeal blood treatment, where a patient's blood is delivered to the patient via a venous hose line, which has a venous puncture cannula or puncture needle, and is removed from the patient via an arterial hose line, which has an arterial puncture cannula or puncture needle. Moreover, the invention relates to a blood treatment apparatus with an extracorporeal blood circuit that has a device for monitoring the arterial and/or venous vascular access. The invention also relates to a method for monitoring a patient access.

BACKGROUND OF THE INVENTION

In the field of medical technology, a large number of apparatuses are known for delivering fluids to a patient or removing fluids from a patient via a hose line. The access to the patient generally takes place with a catheter for introduction into body organs, or a cannula or needle for puncturing vessels. During the examination or treatment, correct access to the patient must be ensured. It is therefore necessary to monitor the patient access.

In extracorporeal blood treatment, there are particularly high demands on reliability of the vascular access In extracorporeal blood treatment, blood is removed from the patient via an arterial hose line that has an arterial puncture cannula, passed through a dialyzer, and delivered back to the patient via a venous blood line that has a venous puncture cannula. Despite regular monitoring of the patient access by hospital staff, there is the risk of the venous puncture cannula slipping out of the patient's blood vessel unnoticed. When the arterial cannula slips out of the patient's artery, air is sucked into the arterial hose line, which leads to a visual and/or optical alarm and to interruption of the treatment on account of air being detected on the machine side. However, when the venous cannula slips out of the patient's vein, blood can freely flow into the surroundings without being readily detected. If the venous cannula slips out and is not detected immediately, the patient could bleed to death.

To solve this problem, many different devices are known. Some of these devices rely on safety devices provided as standard in blood treatment machines and trigger an immediate interruption of the extracorporeal blood circuit in the event of an incorrect vascular access. The safety devices provided as standard in treatment machines are generally based on monitoring the pressure in the extracorporeal blood circuit. In practice, however, it has been shown that the slipping-out of the venous puncture cannula cannot be detected with sufficient reliability solely by monitoring the pressure in the extracorporeal blood circuit. Some known safety devices do have adequate sensitivity, but are overly sensitive to changes in the patient's position, and this often leads to false alarms. Existing blood treatment apparatuses also cannot be readily retrofitted with the known monitoring devices, but rather the retrofitting is an expensive and cost-intensive intervention.

DE 44 32 348 C2 describes a safety device for a hose line conveying blood, wound discharge or infusion, said safety device reacting to a relative change in position of the hose line. The safety device of DE 44 32 348 C2 has a magnet that is fixed to the hose line and a reed contact that is fixed to the patient. If the hose line is tugged, the distance between the magnet and the reed contact changes and an alarm is triggered.

DE 199 53 068 A1 describes a mechanical safety device that can be fixed to the blood line of a dialysis machine. The safety device of DE 199 53 068 has elastically pre-tensioned clamping jaws, which can be held open by a locking bar fixed to the patient's body, and the blood line is placed between the clamping jaws. A change in position of the blood line moves the locking bar, causing the clamping jaws to pinch off the blood line. This leads to a pressure increase in the blood line, which is detected by the standard known devices for monitoring the pressure in dialysis apparatuses. However, fixing the mechanical safety device to the blood line and to the patient is complicated. Additionally, since the clamping jaws pinch off the blood line abruptly, it is not possible to trigger an alarm before the blood treatment is interrupted. Furthermore, the use of inexpensive plastics as a material for factory assembly of the blood line is also problematic due to the creep processes. The clamping jaws should not be under permanent pre-tensioning, but this is only the case when the clamping jaws are closed. However, since the blood line is pinched off when the clamping jaws are closed, the clamping jaws must be under pre-tensioning. If the device is produced from inexpensive plastics, this could lead to a permanent reduction in the pre-tensioning of the clamping jaws and thus to unfitness of the device for use, as a result of the creep process even at room temperature.

SUMMARY OF INVENTION

One objective of the present invention is to provide a device which permits reliable monitoring of a patient access, is easy to handle, inexpensive to produce and capable of being retrofitted at any time.

A further objective of the present invention is to provide a method of monitoring a patient access in a straightforward manner at any time with a high degree of reliability. Moreover, an objective of the present invention is to provide an extracorporeal blood treatment apparatus with a monitoring device for a patient access.

The device and method according to the present invention are based on a loop being formed in the fluid-conveying hose line. It is assumed that slipping-out of the puncture cannula or the catheter is due to pulling forces on the hose line. If the hose line is placed under a tractive load, the loop automatically tightens, which leads to an increased pressure loss in the hose line that can easily be detected.

The known blood treatment apparatuses already include a device for monitoring the pressure in the extracorporeal blood circuit. If the pressure exceeds preset limits, the blood treatment apparatuses can emit an alarm and/or interrupt the blood treatment. The mechanical devices required for this are already present in the known blood treatment apparatuses.

Thus, the present invention matches the preset limiting values for the pressure in the extracorporeal blood circuit to the hose line used.

It is advantageous that not only can a defective patient access easily be detected, but that the formation of a loop can weaken the transfer of tractive forces to the catheter or the cannula. If the hose is placed under tractive load, the loop first tightens, so that the tractive forces are not immediately transferred to the catheter or the cannula. Only when the loop has tightened to such an extent that the hose kinks are tractive forces transferred to the catheter or the cannula. By then, however, the protective mechanism has already started. Even a small kink is sufficient to permit an increase in the pressure loss in the hose line to be reliably detected. Moreover, it is advantageous that the dynamic pressure builds up more quickly with an increasing flow rate of the fluid. This is especially the case when the hose line is made from a flexible material that easily bends.

If the hose length is dimensioned generously to give the patient suitable freedom of movement, only a few false alarms will arise, because negligible tractive forces occur on the hose line with normal movements. In addition, it is possible for the device for supplying and removing the fluid not to be switched off immediately in the event of a malfunction, but merely for an alarm to be triggered. If an alarm is triggered, the hospital staff can remove the kink by returning the hose line into the loop shape without having to interrupt the treatment.

The device according to the present invention, which can be retrofitted to an apparatus for supplying and removing fluids to or from a patient, has means for fixing a segment of the hose line into the form of a loop. In one embodiment of the present invention, the means for fixing a segment of the hose line into a loop can be fitted on an existing hose line. In another embodiment of the present invention, the means for fixing a segment of the hose line into a loop is designed as a one-piece part of the catheter (puncture wing). In another embodiment, the means for fixing a segment of the hose line into a loop can also be a one-piece part of the catheter.

In the first embodiment, the means for fixing a segment of the hose line into a loop has a first fixing element for the detachable fixing of a first hose segment and a second fixing element for the detachable fixing of a second hose segment, whereby the first and second fixing elements are connected to one another. The two fixing elements can be designed differently. With the first fixing element, the fixing means are fixed to a first hose segment of the hose line. A loop is then formed manually in the hose line, whereby the second hose segment at the end of the loop is fixed with the second fixing element. The effect of this is to prevent the hose line from returning into the original shape. If the hose line is fed loosely at least in one of the two fixing elements, the loop can first tighten in the presence of a tractive load until the hose line finally kinks.

In a preferred embodiment, the first fixing element has a clamp, with which the hose segment can preferably be fixed in a clamped fashion. The diameter of the opening of the clamp is preferably slightly smaller than the diameter of the hose line, so that the hose line can easily be clamped, without the hose being pressed together. In a further preferred embodiment, the second fixing element has an eyelet, through which the hose segment can be passed. Since the hose segment is passed loosely through the eyelet, the loop of the hose line is able to tighten under tractive load.

In further preferred embodiment, the hose line is not passed through the eyelet, but is placed into the eyelet from the side. For this purpose, the hose is slightly pinched together when it is placed into the eyelet. The hose line is prevented from slipping out of the eyelet by closing the eyelet with a snap lock.

It is advantageous for the loop to be formed directly behind the puncture cannula or the catheter, since the hose line is generally subjected to less pulling forces at this point when the patient changes position.

The alternative embodiment, where the means for the fixing of a segment of the hose line is a one-piece part of the catheter (puncture wing), has a fixing element for detachably fixing a segment of a hose line, which either is connected or can be connected to the puncture cannula. The segment of the hose line behind the puncture cannula is formed into a loop and the segment of the hose line lying behind the loop is secured with the fixing element. The fixing element is preferably designed in such a way that the segment of the hose line can be fixed detachably. Alternatively, it is possible for the hose line to form a permanent loop at the catheter (puncture wing).

The fixing elements for the hose segment are preferably eyelets, through which the hose segments can be passed, so that the loop can pull tight in the presence of tractive loading. The eyelet is preferably capable of being splayed apart so that the hose line can be inserted. It can be designed, for example, as a clip or the like for the hose line.

BRIEF DESCRIPTION OF DRAWINGS

Various examples of embodiment of the invention are explained in greater detail below by reference to the drawings.

DETAILED DESCRIPTION OF DRAWINGS

Figure 1:
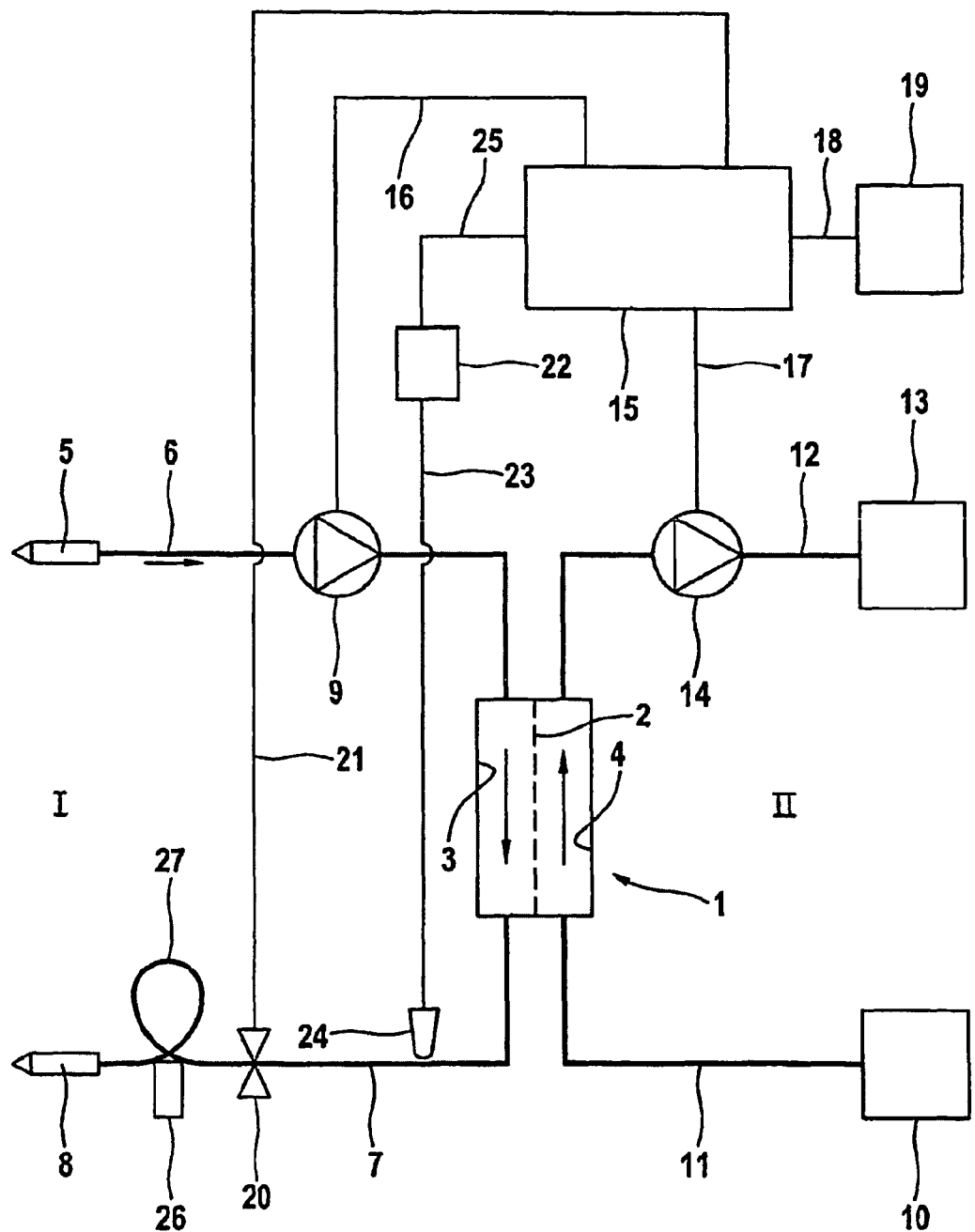
FIG. 1 shows the essential components of a hemodialysis apparatus together with the device according to the invention for the monitoring of the patient access in a simplified diagrammatic representation.

FIG. 1 shows the essential components of a hemodialysis apparatus, which has a device for monitoring a venous vascular access. The hemodialysis apparatus has a dialyzer 1, which is divided by a semi-permeable membrane 2 into a blood chamber 3 and a dialyzing fluid chamber 4. Connected to one of the patient's arteries by means of an arterial puncture cannula 5 is an arterial hose line 6, which leads to the inlet of blood chamber 3 of the dialyzer. Departing from the outlet of blood chamber 3 of dialyzer 1 is a venous hose line 7, which is connected by means of a venous puncture cannula 8 to one of the patient's veins. Arterial hose line 6 is inserted into an occluding blood pump 9, which conveys the blood in extracorporeal blood circuit I.

Dialyzing fluid circuit II of the hemodialysis apparatus includes a dialyzing fluid source 10, to which a dialyzing fluid supply line 11 is connected, which leads to the inlet of dialysing fluid chamber 4 of the dialyzer. Departing from the outlet of dialyzing fluid chamber 4 of dialyzer 1 is a dialyzing fluid discharge line 12, which leads to a drain 13. A dialyzing fluid pump 14 is incorporated into dialyzing fluid discharge line 12.

The control of the dialysis apparatus is assumed by a central control unit 15, which controls blood and dialysing fluid pumps 9, 14 via control lines 16, 17. Central control unit 15 is connected via a data line 18 to an alarm unit 19, which in the event of a malfunction emits an optical and/or acoustic alarm.

Located on venous hose line 7 downstream of blood chamber 3 of dialyzer 1 is an electromagnetically actuatable hose clamp 20, which is closed via a further control line 21 by central control unit 15 if the venous puncture cannula (needle) slips out of the vascular access. Furthermore, control unit 15 stops blood pump 9 after the slipping-out of the cannula.

In order to monitor the pressure in the arterial hose line, the dialysis apparatus has a monitoring device 22, which is connected via a data line 23 to a pressure sensor 24 which measures the pressure in venous hose line 7. Pressure monitoring device 22 communicates with central control unit 15 via a further data line 25.

The device for monitoring the venous vascular access has means 26, described in detail below, for fixing a hose segment of venous hose line 7 in the form of a loop 27. The loop is formed upstream of venous puncture cannula 8 preferably on a segment of the hose line in which the hose line still lies next to the patient's body, for example on his lower arm.

During the dialysis treatment, venous hose line 7 is not subjected to tractive load. Pressure monitoring device 22 measures a pressure P in the venous hose line that lies within preset limits. The typical venous pressures is about 100 to 200 mmHg. It will be assumed that pressure measuring device 22 measures a venous pressure of 150 mmHg. With such pressure conditions, a limiting-value window of about 100 mmHg is defined, whereby the lower limiting value for the pressure lies at 100 mmHg and the upper limiting value at 200 mmHg. If the measured pressure lies above or below the preset limits of 100 and 200 mmHg, central control unit 15 triggers an optical and/or acoustic alarm.

If tugging occurs on venous hose line 7 upstream of loop 27, there is the risk of puncture cannula 8 slipping out of the patient's vein. If this remains unnoticed, the patient's life is at risk. The pressure drop in the venous hose line due to loss of internal pressure in the patient access of about 15 to 25 mmHg may not however lead to the pressure dropping below the lower limiting value for the venous pressure of 100 mmHg. Thus, the slipping-out of the venous puncture cannula is not detected without the monitoring device according to the present invention.

Since the hose line forms a loop 27 above the puncture cannula, the slipping-out of the puncture cannula 8 leads to the triggering of an alarm and/or the interruption of the blood treatment. If tugging occurs on venous hose line 7, loop 27 is first tightened, so that the tractive force can first be "buffered". Further tractive loading, however, leads to a situation where loop 27 is tightened until the hose finally kinks. Since the blood dams up at the kinking point, the venous pressure in the hose line upstream of the kinking point increases. The dynamic pressure depends on the remaining open cross-section of the kinked hose segment at the kinking point and on the blood flow. Pressure measuring device 22 measures the dynamic pressure before the kinking point by means of pressure sensor 24 arranged upstream of loop 27. Within a short time, approximately 1 to 2 seconds, the pressure rises from 150 mmHg on account of the narrowing at the kinking point, and the upper limiting value of 200 mmHg for the venous pressure is exceeded. Consequently, central control unit 15 triggers an alarm and interrupts the blood treatment by closing venous hose clamp 20 and stopping blood pump 9.

Various limiting values of differing levels can be defined for the monitoring, so that it can be deduced whether the puncture cannula risks slipping out of the vascular access or has partially or completely slipped out. Various preliminary alarms or alarms can be triggered when the individual limiting values are exceeded.

When the loop is tightened, a significant change in pressure occurs only relatively late, i.e. only when the kink formation occurs, thus it must be ensured that the hose line does actually kink. It is advantageous to assist this by a constructional or structural anisotropy of the hose line, whereby the shape and/or the constitution of the material of the hose at the kinking point is changed so as to diverge from the shape and/or constitution of the material outside the kinking point. Thus, for example, a predetermined kinking point can be created by the wall of the hose line being thinner or the hose line diverging from the round cross-sectional shape. Thus, a round hose line can have, for example, an elliptical cross-section at the kinking point.

A first embodiment of the means by which a loop can be formed in a straightforward manner in the hose line is described in the following. The fixing means can be fitted at any time to an existing hose line of a conventional dialysis machine, which generally already has a pressure monitoring device that reacts when the pressure falls above or below preset limiting values.

Figure 2:
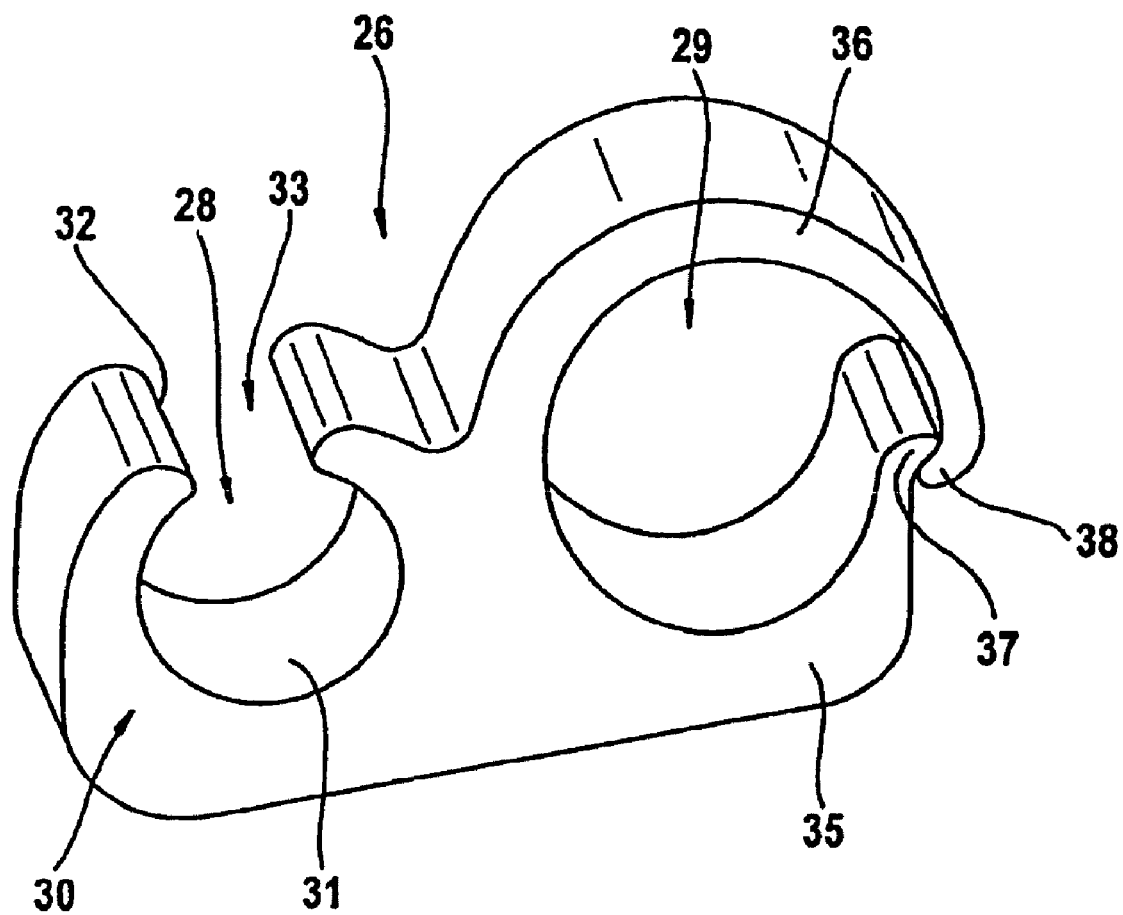
FIG. 2 shows a first embodiment of the device according to the invention in a perspective view.
Figure 3:
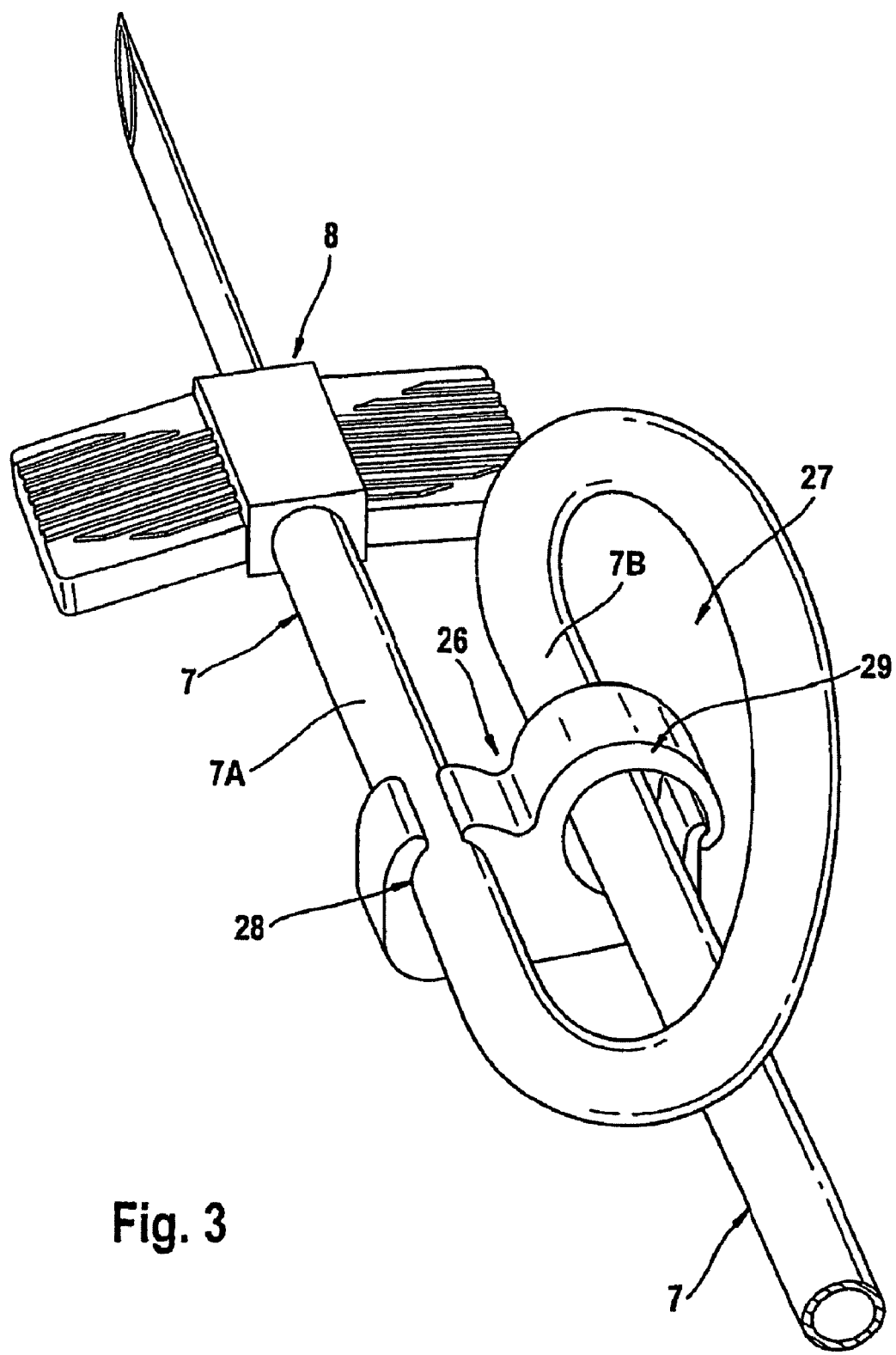
FIG. 3 shows the device from FIG. 2 together with a puncture cannula and a hose line, whereby the hose line has not been subjected to tractive load.
Figure 4:
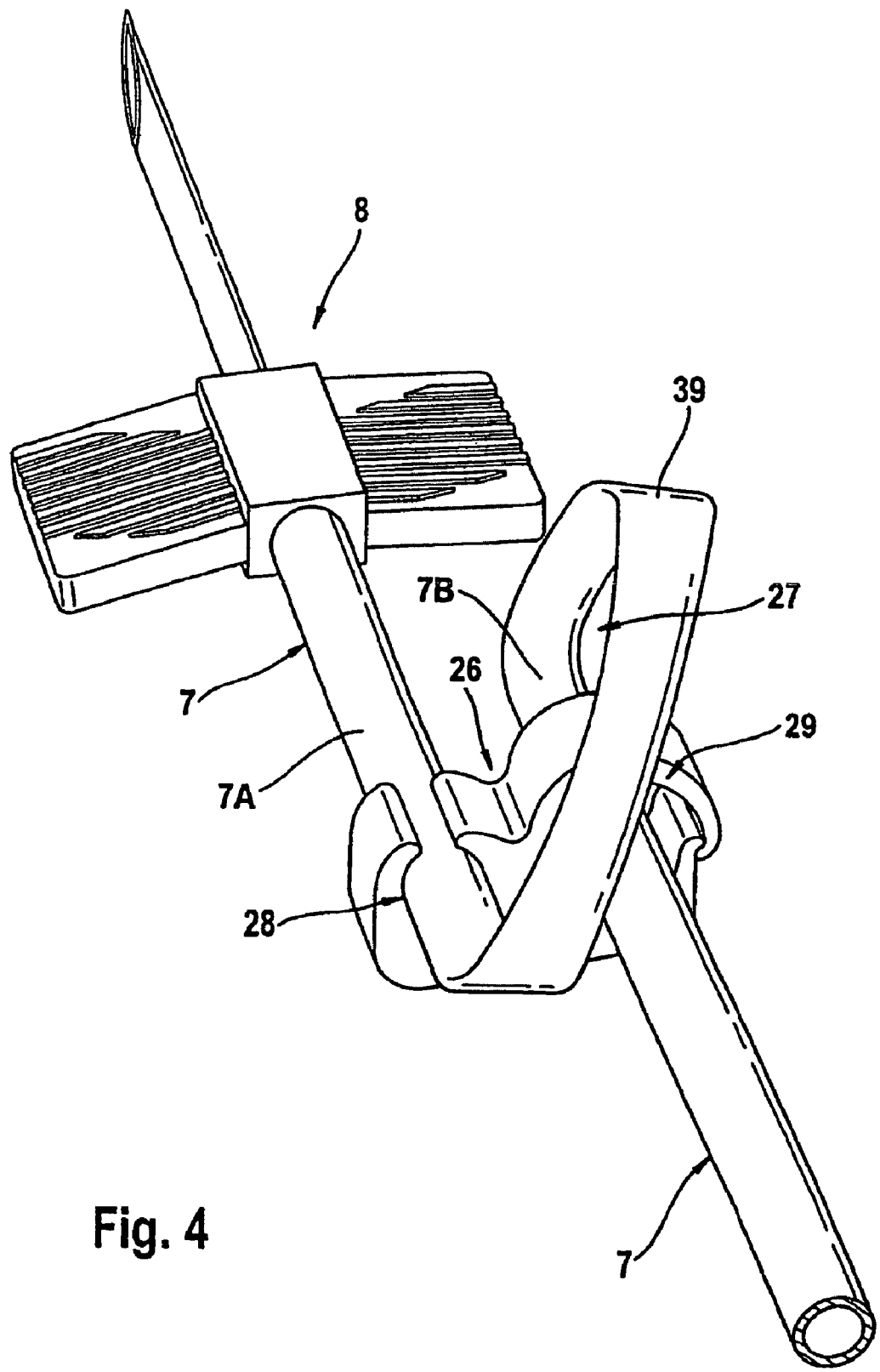
FIG. 4 shows the device from FIG. 2, whereby the hose line has been subjected to tractive load.

FIG. 2 shows fixing means 26 in perspective view without a venous hose line, whilst FIGS. 3 and 4 show fixing means 26 together with the venous hose line, whereby the hose line in FIG. 3 has not been subjected to tractive load and the hose line in FIG. 4 has been subjected to tractive load.

Fixing means 26 has two fixing elements 28, 29 for venous hose line 7. The two fixing elements 28, 29 are arranged so that the hose segments of the hose line held by the fixing elements 28, 29 run parallel to one another. With first fixing element 28, fixing means 26 are fitted on a hose segment 7A of venous hose line 7 that lies upstream of venous puncture cannula 8, preferably directly before the puncture cannula. First fixing element 28 is a plastic injection-moulded part, which is formed in the manner of a clamp 30 into which hose segment 7A can be inserted. Clamp 30 has a central opening 31 with a diameter slightly smaller than the diameter of hose segment 7A, so that the hose segment can be held in a clamped fashion by the surrounding clamp 30. Clamp 30 has an upper gap 33 through which the hose segment 7A is pushed, the upper gap 33 allowing the clamp to be easily splayed apart. Alternatively, in order to fix the fixing means 26 to the hose line 7, two parallel legs can be provided. In this embodiment, the space between the parallel legs is slightly smaller than the diameter of the hose line, so that the hose line can be easily clamped between the two legs.

Formed on first fixing element 28 is a second fixing element 29, which holds a hose segment 7B of venous hose line 7 when the hose line forms a loop 27. Second fixing element 29 is designed as an eyelet, which can be opened or closed. Eyelet 29 is a plastic injection-moulded part with a lower arc-shaped part 35 and an upper arc-shaped part 36. Lower and upper arc-shaped parts 35, 36 each have a locking hook 37, 38, which engage with one another in a snap-in fashion when lower and upper parts 35, 36 are pressed together.

Upper arc-shaped part 36 is bent upwards and eyelet 29 is opened for the insertion of hose segment 7B, so that the hose segment can be inserted into the gap between upper and lower parts 35, 36 into eyelet 29. The eyelet 29 is then closed by pressing together the upper and lower parts 35, 36, so that hose segment 7B is secured in the eyelet 29. The hose segment 7B lies loosely in the eyelet, so that the loop can tighten when tugging occurs on the hose line 7. If tugging occurs on hose line 7, the loop 27 tightens until the hose line kinks at kinking point 39 (FIG. 4).

Figure 5:
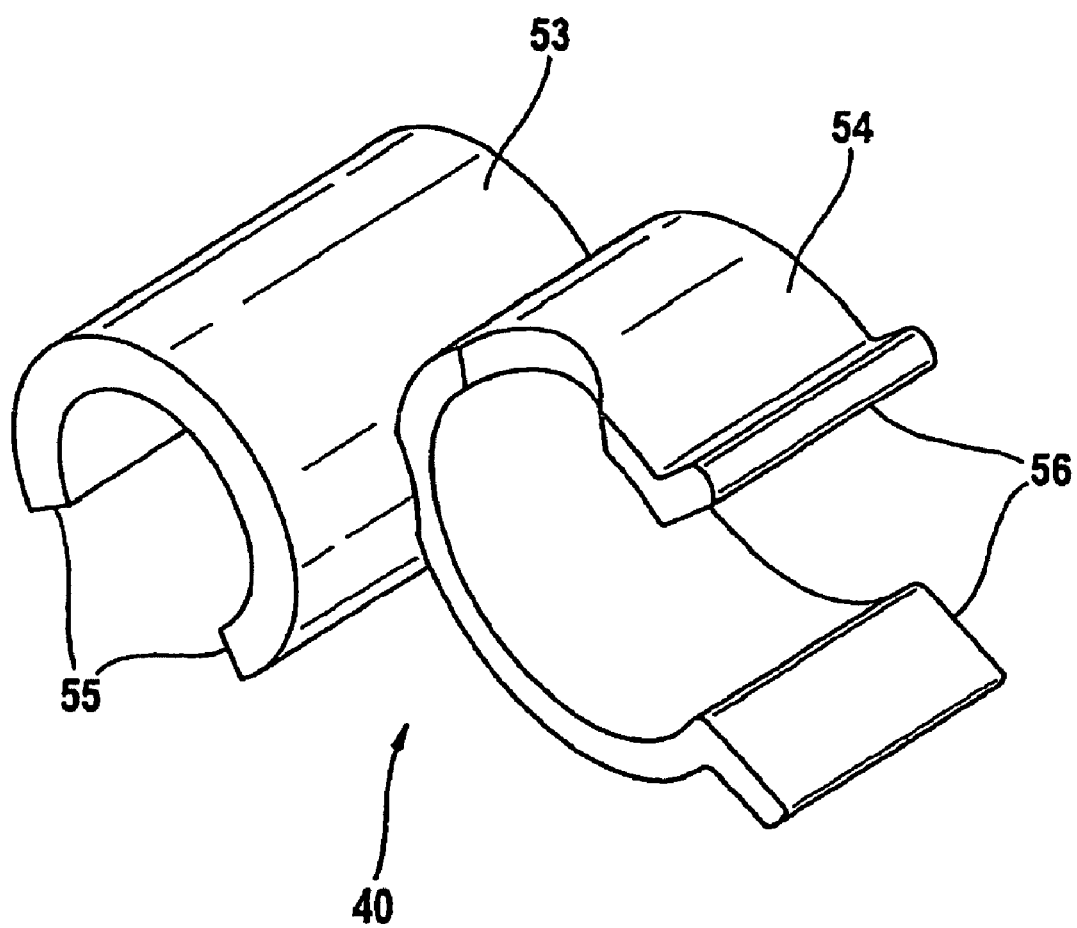
FIG. 5 shows a second embodiment of the device according to the invention in a perspective view.

FIG. 5 shows in perspective view a second embodiment of fixing means 40, which has two eyelets 53, 54 connected together, one of which accommodates first hose segment 7A and the other which accommodates second hose segment 7B. The two eyelets 53, 54 cannot be securely closed, but rather hold the respective hose segment tightly in a slightly clamped fashion. End pieces 55 of the eyelet 53 point inwards, and end pieces 56 of eyelet 54 point outwards. The end pieces of both eyelets, however, can also point inwards or outwards respectively. The end pieces pointing outwards have the advantage that the eyelet can be more easily opened and the hose line inserted more easily.

Figure 6:
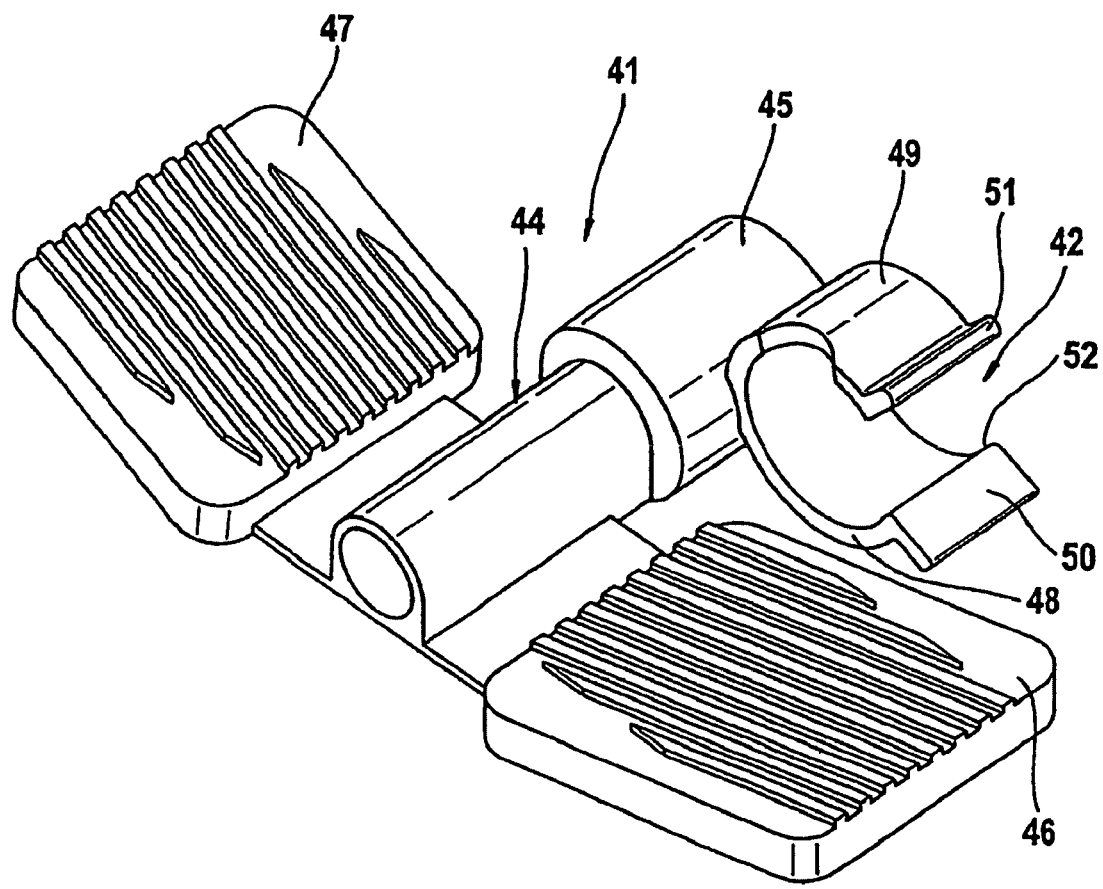
FIG. 6 shows a third embodiment of the device according to the invention in a perspective view.
Figure 7:
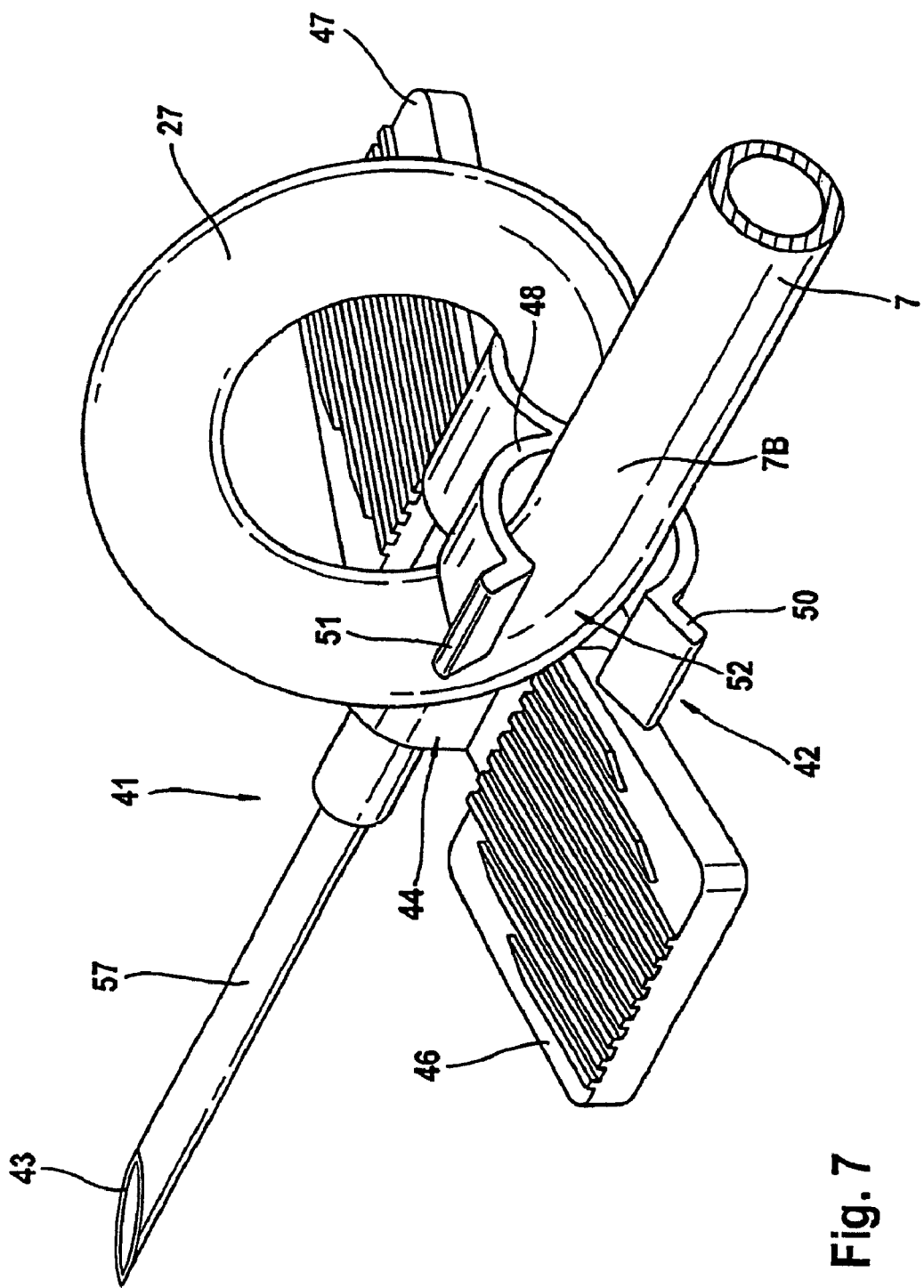
FIG. 7 shows the device from FIG. 6 together with a hose line in a perspective view.
Figure 8:
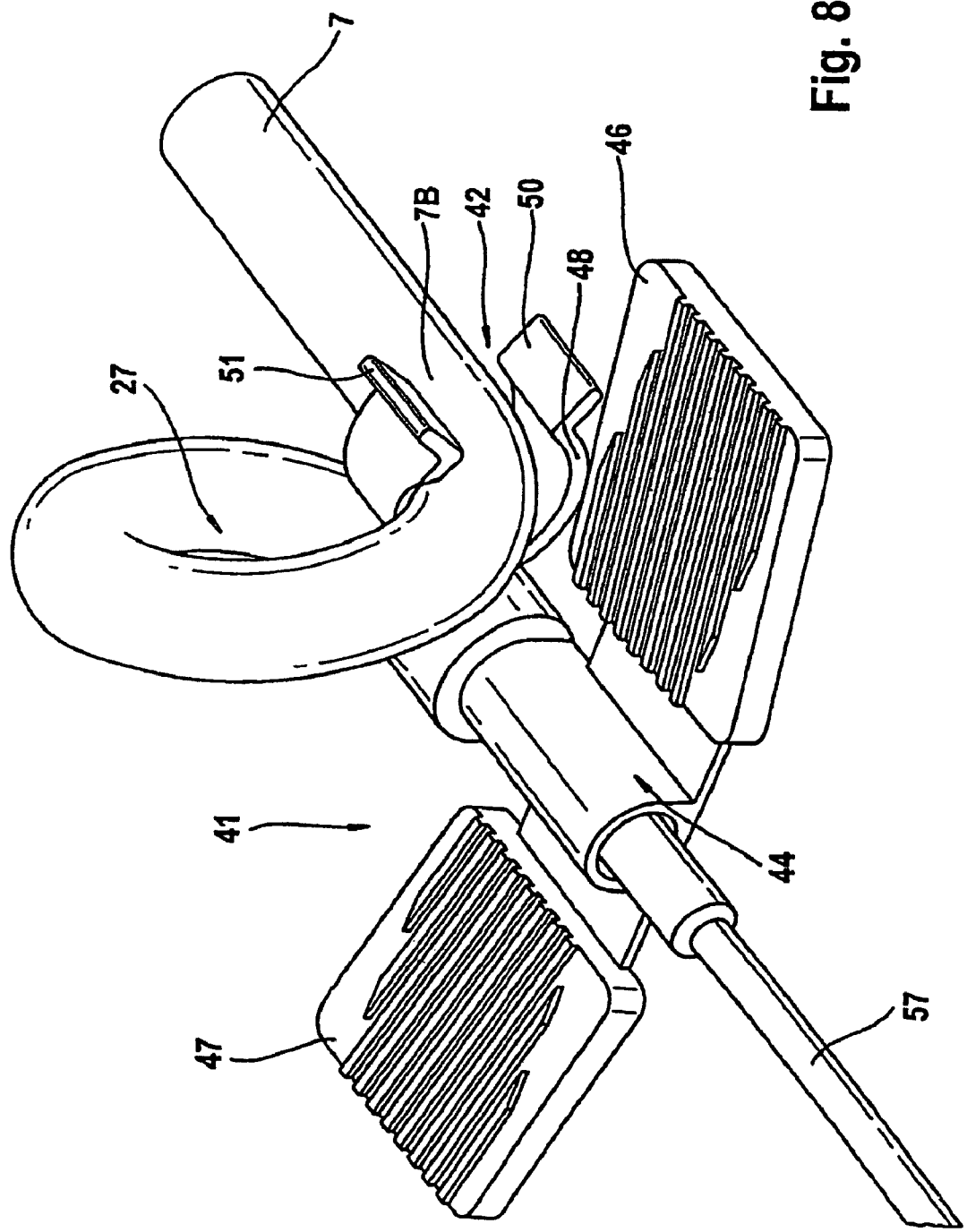
FIG. 8 shows a further view of the device from FIG. 6 in a perspective view.

FIGS. 6 to 8 show perspective views from different directions of further alternative embodiments of fixing means 41. In this embodiment, the fixing means are designed as a puncture wing 41. The puncture wing 41 has a fixing element 42 for the detachable fixing of a hose segment 7B of a hose line 7 connected or connectable to the cannula. Puncture wing 41 has a cannula needle 57 with a ground-section opening 43 and a hose connection piece 44, to which hose line 7 is firmly connected, for example by gluing or welding. For the connection of the hose line, hose connection piece 44 and the end of the hose line can also be provided with suitable connectors. FIG. 6 does not show the puncture cannula which is inserted into the hose connection piece.

Hose connection piece 44 has a cylindrical body 45 for receiving the hose end piece, with wings 46, 47 formed on both sides thereof. Fixing element 42 is connected to cylindrical body 45 of hose connection piece 44. Fixing element 42 is an eyelet that can be opened and hose segment 7B of hose line 7 can be pushed into the eyelet 42 from the side after the formation of loop 27. The eyelet 42 comprises two arc-shaped plastic pieces 48, 49, which are formed at the side on the hose connection piece 44, and each arc shaped piece 48, 49 ends in a leg 50, 51 bent off at an angle. After formation of loop 27, hose line 7 is inserted through gap 52 between the two legs 50, 51 from the side into the eyelet 42. The hose line 7 is passed loosely in the eyelet 42, so that the loop can tighten and kink under tractive loading.

The invention claimed is:

1. A device for monitoring vascular access in extracorporeal blood treatment comprising:
 a hose line having a lumen therethrough, a first segment, and a second segment,
 a first fixing element tightly receiving the first segment of the hose line, and
 a second fixing element loosely receiving the second segment of the hose line,
 wherein said first segment of the hose line enters a first side of the first fixing element, and said second segment of the hose line enters a first side of the second fixing element such that a loop is formed in the hose line between the first fixing element and the second fixing element,
 wherein the first segment is received in the first fixing element from a first direction and the second segment is received in the second fixing element from the same first direction.

2. The device of claim 1, wherein the first fixing element has a C-shape comprising a curved central portion and two end pieces defining a gap therebetween for receiving the hose line.

3. The device of claim 2, wherein the second fixing element has a C-shape comprising a curved central portion and two end pieces defining a gap therebetween for receiving the hose line.

4. The device of claim 3, wherein the two end pieces of at least one of the first fixing element or second fixing element extend at an angle outwardly from the C-shape.

5. The device of claim 2, wherein the second fixing element has an upper semi-circular portion and a lower semi-circular portion.

6. The device of claim 5, wherein the upper semi-circular portion has a first locking portion and the lower semicircular portion has a second locking portion,
 the first locking portion and the second locking portion capable of unlocking in an open position to receive the hose line, and
 the first locking portion and the second locking portion capable of locking together in a closed position to hold the hose line.

7. The device of claim 1, wherein the first fixing element and the second fixing element are connected.

8. The device of claim 1, wherein the first fixing element has a first opening for receiving the first segment of hose line, and the second fixing element has a second opening for receiving the second segment of hose line, and the first opening is smaller than the second opening.

9. The device of claim 8, wherein a diameter of the first opening is smaller than a diameter of the second opening.

10. The device of claim 1, wherein the loop can tighten when a tractive force is applied to the second segment of the hose.

11. The device of claim 10, wherein when the loop tightens, the pressure in the hose line can increase above a pre-set limit.

12. The device of claim 1, wherein the loop in the hose line further comprises a predetermined kinking point.

13. The device of claim 12, wherein the predetermined kinking point has a first wall thickness and the rest of the first segment and the second segment has a second wall thickness, and the first wall thickness is less than the second wall thickness.

14. The device of claim 12, wherein the predetermined kinking point has a non-round cross-section and the rest of the first segment and the second segment has a round cross-section.

15. The device of claim 1, wherein the first segment forming the loop overlaps the second segment forming the loop as the second segment exits from the second fixing element on a second side.

16. A blood treatment apparatus comprising:
 an extracorporeal blood circuit having an arterial hose line with an arterial puncture cannula, and a venous hose line with a venous puncture cannula; and
 a device for monitoring the pressure in the arterial hose line, the venous hose line, or both, said device comprising:
 a first fixing element tightly receiving a first segment of the arterial hose line or the venous hose line, and a second fixing element loosely receiving a second segment of the arterial hose line or the venous hose line, wherein said first segment of the arterial hose line or the venous hose line enters a first side of the first fixing element from a first direction, and said second segment of the arterial hose line or the venous hose line enters a first side of the second fixing element from the same first direction such that a loop is formed in the hose line between the first fixing element and the second fixing element, wherein the device is configured to determine if the venous puncture cannula or the arterial puncture cannula has slipped out when there is a change in the pressure outside a preset limiting range on account of a tractive loading of the arterial hose line or the venous hose line.

17. The device of claim 1, wherein the loop extends from a second side of the first fixing element to the first side of the second fixing element.

18. A method for monitoring an access to a patient for supplying or carrying away a fluid to or from the patient via a hose line, said method comprising:

using a device for monitoring vascular access in extracorporeal blood treatment comprising: a hose line having a lumen therethrough, a first segment, and a second segment; a first fixing element; and a second fixing element;

tightly receiving the first segment of the hose line in the first fixing element;

loosely receiving the second segment of the hose line in the second fixing element;

forming a loop in the hose line between the first fixing element and the second fixing element, wherein said first segment of the hose line enters a first side of the first fixing element from a first direction, and said second segment of the hose line enters a first side of the second fixing element from the same first direction;

monitoring a pressure in the hose line; and determining that there is an incorrect patient access when the monitored pressure is outside of a preset limiting range.

19. The method of claim 18, wherein the hose line includes a predetermined kinking point, further comprising:

applying a tractive load to the hose line; and kinking the hose line at the predetermined kinking point.

* * * * *